(12) United States Patent
Fukuzawa

(10) Patent No.: US 9,250,184 B2
(45) Date of Patent: Feb. 2, 2016

(54) STATUS ESTIMATION DEVICE, STATUS ESTIMATION METHOD AND PROGRAM FOR ULTRAVIOLET CURABLE RESIN

(75) Inventor: Takashi Fukuzawa, Minato-ku (JP)

(73) Assignee: Nippon Sheet Glass Company, Limited, Tokyo (JP)

(*) Notice: Subject to any disclaimer, the term of this patent is extended or adjusted under 35 U.S.C. 154(b) by 1050 days.

(21) Appl. No.: 13/243,611

(22) Filed: Sep. 23, 2011

(65) Prior Publication Data

US 2012/0077895 A1 Mar. 29, 2012

(30) Foreign Application Priority Data

Sep. 24, 2010 (JP) ................................. 2010-213732

(51) Int. Cl.
*G01N 21/64* (2006.01)
*B01J 19/12* (2006.01)

(52) U.S. Cl.
CPC ............... *G01N 21/64* (2013.01); *B01J 19/123* (2013.01); *B01J 2219/002* (2013.01); *B01J 2219/0024* (2013.01); *B01J 2219/00213* (2013.01); *B01J 2219/0879* (2013.01); *G01N 2021/6417* (2013.01); *G01N 2021/6484* (2013.01)

(58) Field of Classification Search
CPC ............ C08J 3/28; B01J 19/08; B01J 19/123; B01J 2219/00213; B01J 2219/0879; B01J 2219/0024; B01J 2219/002; G01N 21/64; G01N 2021/6417; G01N 2021/6484
USPC .......................... 250/252.1, 459.1, 458.1, 372; 422/186.3; 522/1
See application file for complete search history.

(56) References Cited

U.S. PATENT DOCUMENTS

| | | | | |
|---|---|---|---|---|
| 5,100,802 | A * | 3/1992 | Mickols | 436/34 |
| 5,598,005 | A * | 1/1997 | Wang et al. | 250/459.1 |
| 5,606,171 | A * | 2/1997 | Neckers et al. | 250/459.1 |
| 5,955,002 | A * | 9/1999 | Neckers et al. | 252/301.35 |
| 2005/0143483 | A1 * | 6/2005 | Sanuki et al. | 522/99 |
| 2008/0124247 | A1 * | 5/2008 | Matsuoka | G01N 21/645 422/82.08 |
| 2008/0225270 | A1 * | 9/2008 | Senga et al. | 356/51 |
| 2008/0315118 | A1 * | 12/2008 | Anraku | G01J 3/02 250/458.1 |

(Continued)

FOREIGN PATENT DOCUMENTS

| | | | | |
|---|---|---|---|---|
| JP | 2000055806 | A * | 2/2000 | G01N 21/35 |
| JP | 2007-248244 | A | 9/2007 | |

(Continued)

OTHER PUBLICATIONS

Office Action issued in corresponding Japanese Patent Application No. 2010-213732 dated Nov. 12, 2013.

*Primary Examiner* — David Porta
*Assistant Examiner* — Gisselle Gutierrez
(74) *Attorney, Agent, or Firm* — Sughrue Mion, PLLC

(57) ABSTRACT

A status estimation device for ultraviolet curable resin includes a probe configured to irradiate an ultraviolet curable resin with excitation light, a wavelength demultiplexer configured to receive fluorescence produced from the ultraviolet curable resin and detect spectral distribution of the fluorescence, and a computer configured to estimate status of the ultraviolet curable resin by comparing a shape of pre-irradiation spectral distribution detected when the ultraviolet curable resin is irradiated by excitation light before being irradiated by ultraviolet radiation with a shape of post-irradiation spectral distribution detected when the ultraviolet curable resin is irradiated by excitation light after being irradiated by ultraviolet radiation.

11 Claims, 11 Drawing Sheets

(56) References Cited

U.S. PATENT DOCUMENTS

| | | | |
|---|---|---|---|
| 2010/0224793 A1* | 9/2010 | Fukuzawa | G01N 21/645 250/458.1 |
| 2010/0243915 A1* | 9/2010 | Fukuzawa | G01N 21/645 250/458.1 |
| 2010/0294948 A1* | 11/2010 | Fukuzawa | G01N 21/645 250/458.1 |

FOREIGN PATENT DOCUMENTS

| JP | WO2008066054 | * | 6/2008 | G01N 21/64 |
|---|---|---|---|---|
| JP | 2009-075002 A | | 4/2009 | |

* cited by examiner

STATUS ESTIMATION DEVICE, STATUS ESTIMATION METHOD AND PROGRAM FOR ULTRAVIOLET CURABLE RESIN

BACKGROUND OF THE INVENTION

1. Field of the Invention

The present invention relates to devices, methods, and programs for estimating the status of an ultraviolet curable resin.

2. Description of the Related Art

Ultraviolet curable resin has been used as adhesive in assembling optical devices and electronic devices. Because it is difficult to measure the cure degree of ultraviolet curable resin by visual inspection, measurement is normally done by destructive inspection. In cases where an ultraviolet curable resin is used in a factory line, the cure degree is indirectly managed by managing the luminance of curing ultraviolet radiation and time of irradiation and by conducting a destructive test on a sample by sampling inspection.

Recently, a nondestructive inspection method is known whereby the status, i.e., the cure degree, of an ultraviolet curable resin is estimated based on time-dependent change in the intensity of fluorescence produced when the ultraviolet curable resin is irradiated by ultraviolet radiation (see, for example, patent document No. 1).

[patent document No. 1] JP 2007-248244

However, the intensity of fluorescence from some ultraviolet curable resins changes with an elapse of time after curing. Therefore, the method disclosed in patent document No. 1 may only be capable of accurately estimating the status of an ultraviolet curable resin immediately after the resin is irradiated by ultraviolet radiation.

Further, since the fluorescence intensity varies depending on the amount of coating made of ultraviolet curable resin, the method disclosed in patent document No. 1 may not be able to estimate the status of the ultraviolet resin with high precision.

SUMMARY OF THE INVENTION

The present invention addresses the background as described above and a purpose thereof is to provide a technology capable of estimating the status of an ultraviolet curable resin with high precision.

In order to address the above-mentioned problem the status estimation device for ultraviolet curable resin according to one embodiment of the present invention comprises; an irradiation unit configured to irradiate an ultraviolet curable resin with excitation light; a detection unit configured to receive fluorescence produced from the ultraviolet curable resin and detect wavelength characteristics of the fluorescence; and an estimation unit configured to estimate status of the ultraviolet curable resin based on the wavelength characteristics of the fluorescence.

According to the embodiment, by estimating the status of the ultraviolet curable resin based on the wavelength characteristics of the fluorescence, the status can be estimated with higher precision than based on the fluorescence intensity. The term "wavelength characteristics" means fluorescence intensity at two wavelengths or more.

The detection unit may detect spectral distribution of the fluorescence, and the estimation unit may estimate the status of the ultraviolet curable resin based on a shape of the detected spectral distribution. Spectral distribution may be considered as indication of fluorescence intensity at a large number of wavelengths.

The estimation unit may estimate the status of the ultraviolet curable resin by comparing the shape of pre-irradiation spectral distribution detected when the ultraviolet curable resin is irradiated by excitation light before being irradiated by ultraviolet radiation with the shape of post-irradiation spectral distribution detected when the ultraviolet curable resin is irradiated by excitation light after being irradiated by ultraviolet radiation.

The estimation unit may estimate the status of the ultraviolet curable resin by comparing the shape of normalized pre-irradiation spectral distribution with the shape of normalized post-irradiation spectral distribution.

The estimation unit may estimate that the ultraviolet curable resin has reached a predetermined cure degree if the shape of post-irradiation spectral distribution differs from that of pre-irradiation spectral distribution.

The estimation unit may estimate that the ultraviolet curable resin has reached a predetermined cure degree if the post-irradiation spectral distribution detected when the ultraviolet curable resin is irradiated by excitation light after being irradiated by ultraviolet radiation exhibits a predetermined shape.

The detection unit may detect a first intensity at a first wavelength of the fluorescence and a second intensity at a second wavelength of the fluorescence, and the estimation unit may estimate the status of the ultraviolet curable resin based on the intensity ratio of the second intensity with respect to the first intensity.

The estimation unit may estimate the status of the ultraviolet curable resin by comparing pre-irradiation intensity ratio detected when the ultraviolet curable resin is irradiated by excitation light before being irradiated by ultraviolet radiation with post-irradiation intensity ratio detected when the ultraviolet curable resin is irradiated by excitation light after being irradiated by ultraviolet radiation.

The estimation unit may estimate that the ultraviolet curable resin has reached a predetermined cure degree if the post-irradiation intensity ratio differs in value from the pre-irradiation intensity ratio.

The estimation unit may estimate that the ultraviolet curable resin has reached a predetermined cure degree if the post-irradiation intensity ratio detected when the ultraviolet curable resin is irradiated by excitation light after being irradiated by ultraviolet radiation is a predetermined intensity ratio.

Another embodiment of the present invention relates to a status estimation method for ultraviolet curable resin. The method comprises: irradiating an ultraviolet curable resin with excitation light; receiving fluorescence produced from the ultraviolet curable resin and detecting wavelength characteristics of the fluorescence; and estimating status of the ultraviolet curable resin based on the wavelength characteristics of the fluorescence.

Still another embodiment of the present invention relates to a program that causes a computer to estimate status of an ultraviolet curable resin. The program comprises a module configured to receive wavelength characteristics of fluorescence produced from an ultraviolet curable resin irradiated with excitation light and a module configured to estimate status of the ultraviolet curable resin based on the wavelength characteristics of the fluorescence.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which.

DETAILED DESCRIPTION OF THE INVENTION

The invention will now be described by reference to the preferred embodiments. This does not intend to limit the scope of the present invention, but to exemplify the invention.

A description will be given below of a status estimation device for estimating the status of an ultraviolet curable resin according to an embodiment of the present invention.

Figure 1:
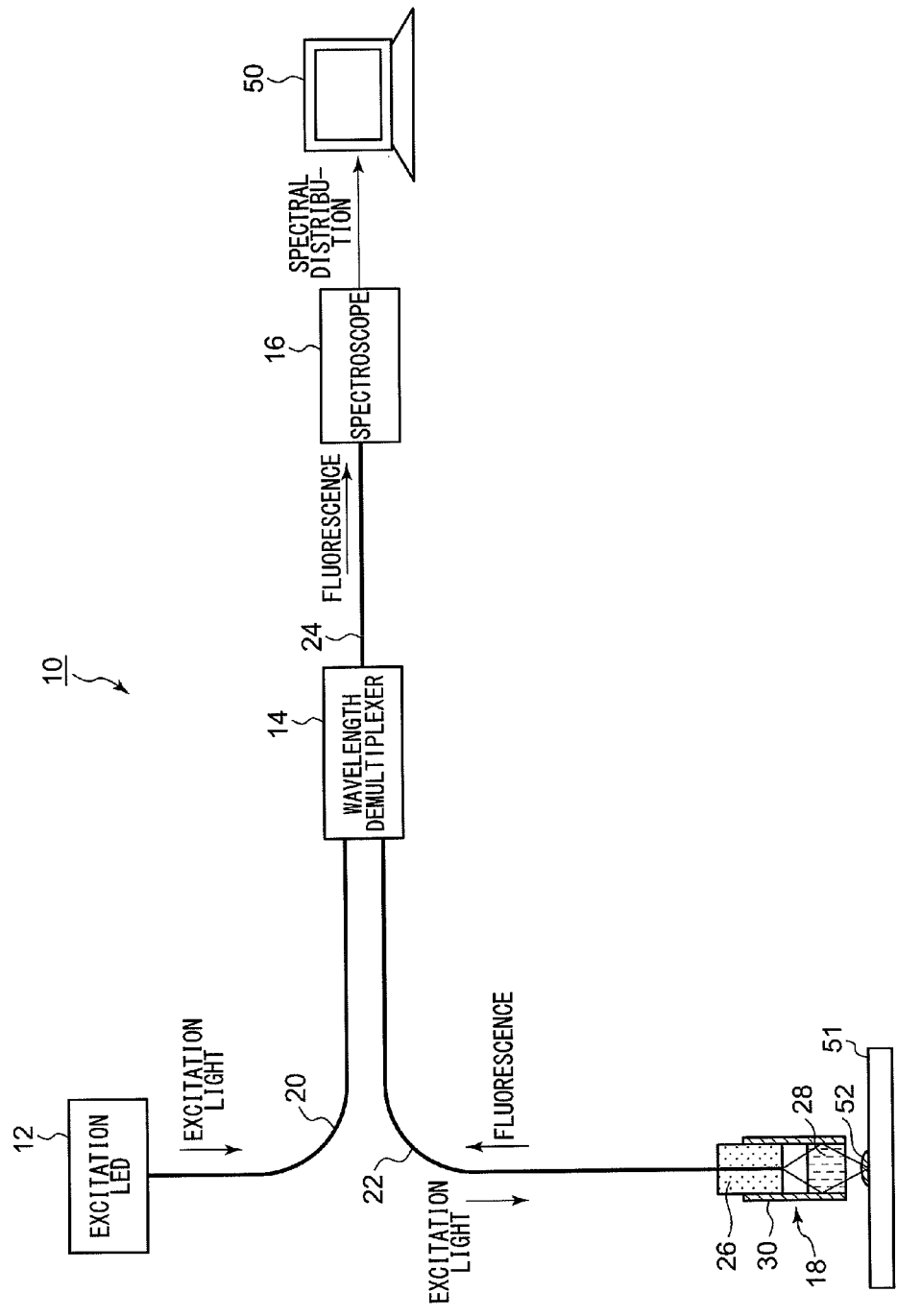
FIG. 1 shows the ultraviolet curable resin status estimation device according to the first embodiment of the present invention.

FIG. 1 shows an ultraviolet curable resin status estimation device 10 according to the first embodiment of the present invention. The status estimation device 10 is a device for measuring the status of an ultraviolet curable resin 52 applied on a substrate 51, i.e., the cure degree of the ultraviolet curable resin 52.

As shown in FIG. 1, the status estimation device 10 comprises an excitation LED 12, a wavelength demultiplexer 14, a spectroscope 16, a probe 18, a first optical fiber 20 connecting the excitation LED 12 and the wavelength demultiplexer 14, a second optical fiber 22 connecting the wavelength demultiplexer 14 and the probe 18, a third optical fiber 24 connecting the wavelength demultiplexer 14 and the spectroscope 16, and a computer 50 connected to the spectroscope 16.

The excitation LED 12 is for emitting excitation light for irradiating the ultraviolet curable resin subject to measurement. For example, the excitation LED 12 may emit light of a primary wavelength $\lambda 1=370$ nm. A bandpass filter with a passband of 352-388 nm may be provided subsequent to the excitation LED 12. The excitation light emitted from the excitation LED 12 is propagated to the wavelength demultiplexer 14 via the first optical filter 12. An optical fiber of silica glass is suitably used as the first optical fiber 20 so that the excitation light of a primary wavelength $\lambda 1=370$ nm can be transmitted with low loss.

The excitation light incident on the wavelength demultiplexer 14 is guided to the second optical fiber 22 in the wavelength demultiplexer 14, propagated through the second optical fiber 22, and emitted from the probe 18 fitted to the end of the second optical fiber 22. Like the first optical fiber 20, an optical fiber of silica glass is suitably used as the second optical fiber 22.

The probe 18 comprises: a ferrule 26 for retaining the end of the second optical fiber 22; a lens 28 for condensing the excitation light emitted from the end of the second optical fiber 22 and irradiating the condensed light to the front focal point and for condensing the light produced at the front focal point and guiding the condensed light to the second optical fiber 22; and a cylindrical securing member 30 for securing the ferrule 26 and the lens 28. The lens 28 may be implemented by using a rod lens designed to produce an equal-magnification image at the end face of the second optical lens 22. The lens 28 may comprise a plurality of lenses. When the ultraviolet curable resin 52 is located at the front focal point of the lens 28, fluorescence is produced from the ultraviolet curable resin 52 as the ultraviolet curable resin 52 is irradiated by the excitation light from the lens 28. The fluorescence is condensed by the lens 28 and is incident on the end of the second optical fiber 22 located at the rear focal point of the lens 28. The reflected light derived from the excitation light is condensed by the lens 28 and incident on the second optical fiber 22.

The fluorescence and the reflected light incident on the second optical fiber 22 are propagated through the second optical fiber 22 and incident on the wavelength demultiplexer 14. The fluorescence is guided to the third optical fiber 24 in the wavelength demultiplexer 14. The fluorescence propagated through the third optical fiber 24 is received by the spectroscope 16.

The spectroscope 16 measures the spectral distribution of the received fluorescence. Spectral distribution represents continuous variation in intensity according to the wavelength of light. Spectral distribution is generally represented by a graph in which the horizontal axis represents wavelength and the vertical axis represents intensity at each wavelength. The spectroscope 16 may be implemented by using a grating and a linear sensor. Alternatively, the spectroscope 16 may be implemented by a linear variable filter (LVF), characterized by a passband that varies depending on the position, and a PD or APD. Information on spectral distribution is transmitted to a computer 50. The computer 50 estimates the status of the ultraviolet curable resin based on the received spectral distribution. The method for estimation will be described in detail below.

Figure 2:
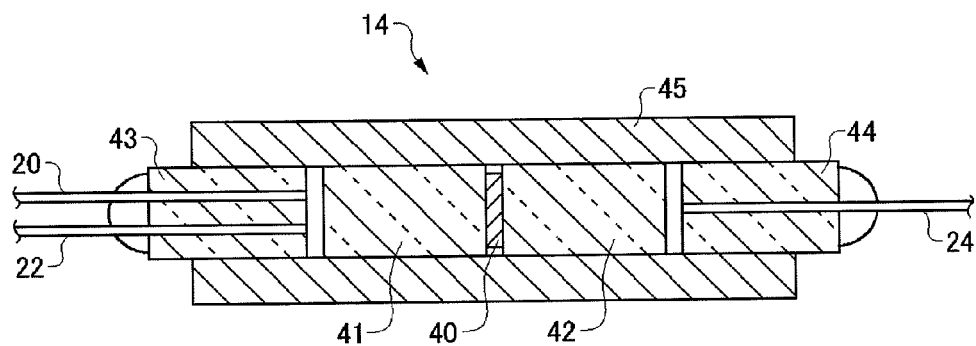
FIG. 2 shows an exemplary schematic structure of the wavelength demultiplexer.

FIG. 2 shows an exemplary schematic structure of the wavelength demultiplexer 14. The wavelength demultiplexer 14 comprises a wavelength demultiplexing filter 40, first and second lenses 41 and 42 provided to sandwich the wavelength demultiplexing filter 40, a first capillary 43 configured to retain the first and second optical fibers 20 and 22 and provided to face the first lens 41, and a second capillary 44 configured to retain the third optical fiber 24 and provided to face the second lens 42, the first and second lenses 41 and 42, and the first and second capillaries 43 and 44 being retained by a cylindrical retention member 45.

The first and second capillaries 43 and 44 may be implemented by using, for example, a glass-based material comprising, for example, borosilicate glass.

Each of the first and second lenses 41 and 42 may be implemented by using a gradient index cylindrical rod lens in which the refractive index is graded to drop from the center toward the outer periphery. By using a gradient index cylindrical lens, the two end faces at the input and output are formed as planes perpendicular to the light axis direction, facilitating assembly such as coupling of lenses. Since the gradient index cylindrical lens is configured to be cylindrical in shape, the lens can be easily accommodated in the retention member 45, facilitating alignment of light axes. The first and second lenses 41 and 42 may be implemented by using a drum lens. A drum lens is formed into the shape of a bale by polishing the middle of a ball lens.

The wavelength demultiplexing filter 40 functions as a wavelength selective member reflecting excitation light and transmitting fluorescence. Generally, the primary wavelength λ1 of excitation light and the primary wavelength λ2 of fluorescence are related such that λ1<λ2. Therefore, it is necessary for the cutoff wavelength λoff of the wavelength demultiplexing filter 40 to be larger than λ1 and smaller than λ2. For example, if the primary wavelength λ1=370 nm, the wavelength demultiplexing filter 40 may be implemented by using a bandpass filter with a passband of 420-500 nm.

More specifically, the wavelength demultiplexer 40 may be implemented by using a dielectric multilayer film formed of a stack of a layer comprising, for example, $SiO_2$, characterized by a low refractive index, and layers comprising, for example, $TiO_2$, $ZrO_2$, and $Ta_2O_5$, characterized by a high refractive index. Preferably, the transmission characteristics of the wavelength demultiplexing filter 40 be such that the transmittance of light of a wavelength shorter than the cutoff wavelength λoff is −30 dB or lower (0.1%) and the transmittance of light of a wavelength longer than λoff be −3 dB or higher (97-50%).

By using the wavelength demultiplexing filter 40 as described above, the excitation light with the primary wavelength λ1 emitted from the excitation LED 12 is reflected by the wavelength demultiplexing filter 40 and guided to the second optical fiber 22 since the transmittance of the excitation light through the wavelength demultiplexing filter 40 is −30 dB or lower. This can properly prevent the transmittance of the excitation light through the wavelength demultiplexer 14 so that the level of noise incurred when measuring/sensing fluorescence is efficiently reduced.

Meanwhile, the lights guided to the wavelength demultiplexer 14 via the probe 18 and the second optical fiber 22 include the reflection of the excitation light having the primary wavelength λ1 and the fluorescence having the primary wavelength λ2. Of these lights, the reflected light is reflected by the wavelength demultiplexing filter 40, like the excitation light from the excitation LED 12. The fluorescence is transmitted in the wavelength demultiplexing filter 40 and incident on the second lens 42 since the transmittance of the fluorescence through the wavelength demultiplexing filter 40 is −3 dB or higher. The fluorescence is then guided by the second lens 42 to the third optical fiber 24. This secures the intensity of a detection signal indicating the fluorescence transmitted in the wavelength demultiplexer 14.

Figure 3:
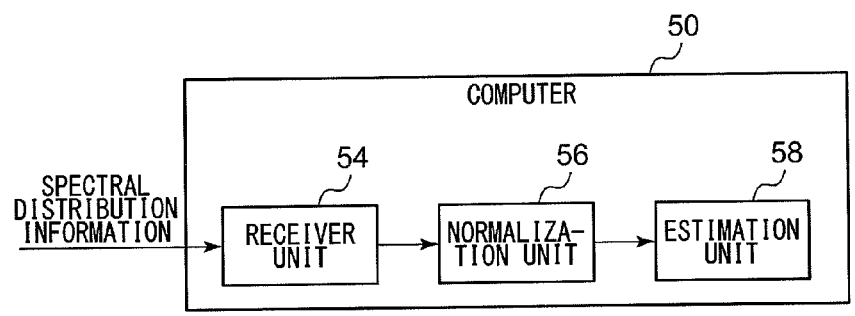
FIG. 3 shows functional blocks of the computer according to the first embodiment.

FIG. 3 shows functional blocks of the computer 50 according to the first embodiment. As shown in FIG. 3, the computer 50 comprises a receiver 54, a normalization unit 56, and an estimation unit 58. The blocks depicted in the block diagram of this specification are implemented in hardware such as devices or mechanical components like a CPU of a computer, and in software such as a computer program etc. FIG. 3 depicts functional blocks implemented by the cooperation of these elements. Therefore, it will be obvious to those skilled in the art that the functional blocks may be implemented in a variety of manners by hardware only, software only, or a combination of thereof.

The receiver unit 54 receives spectral distribution information from the spectroscope 16. The normalization unit 56 normalizes the spectral distribution. The estimation unit 58 estimates the status of the ultraviolet curable resin 52 based on the shape of the normalized spectral distribution.

More specifically, the estimation unit 58 compares the pre-irradiation spectral distribution detected when the ultraviolet curable resin 52 is illuminated by the excitation light before the resin is irradiated by ultraviolet radiation with the post-irradiation spectral distribution detected when the ultraviolet curable resin 52 is illuminated by the excitation light after the resin is irradiated by ultraviolet radiation. If the post-irradiation spectral distribution is of a shape different from the pre-irradiation spectral distribution, the estimation unit 58 estimates that the ultraviolet curable resin 52 has reached a predetermined cure degree. The pre-irradiation spectral distribution may be stored in a memory of the computer 50.

A description will now be given of the status estimation device 10 based on specific examples.

Figure 4:
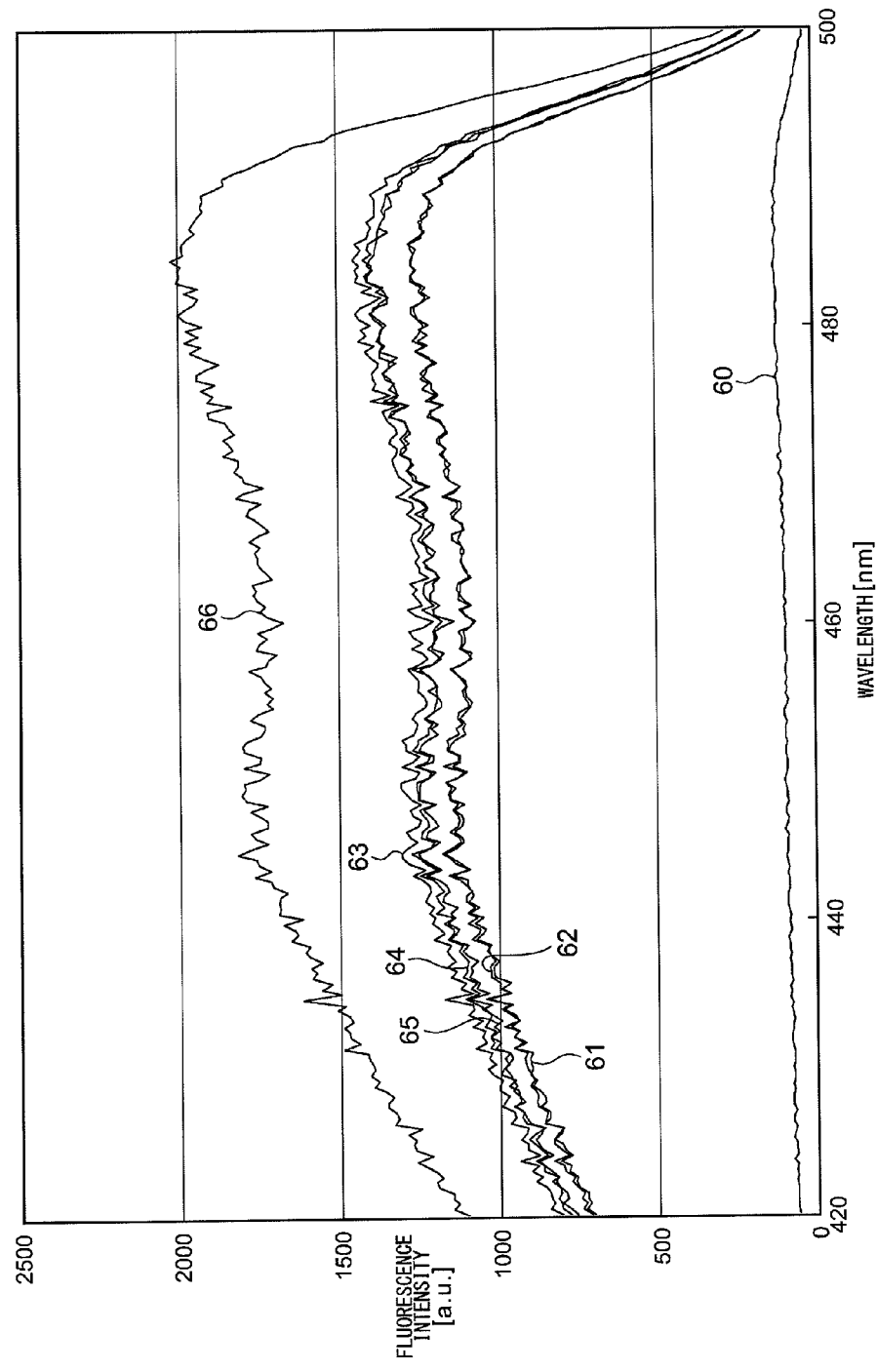
FIG. 4 shows an exemplary spectral distribution.

FIG. 4 shows an exemplary spectral distribution. FIG. 4 shows a spectral distribution obtained when the ultraviolet resin 52 is implemented by using World Rock 8774 (hereinafter, referred to as a sample 1) from Kyoritsu Chemical & co., ltd. Referring to FIG. 4, the horizontal axis represents wavelength (nm) and the vertical axis represents fluorescence intensity (in arbitrary unit). Referring to FIG. 4, a curve 60 represents a spectral distribution occurring before the resin is irradiated by curing ultraviolet radiation i.e., before the resin is cured, a curve 61 represents a spectral distribution occurring after the resin is irradiated by curing ultraviolet radiation for 30 seconds, a curve 62 represents a spectral distribution occurring after the resin is irradiated by curing ultraviolet radiation for 60 seconds, a curve 63 represents a spectral distribution occurring after the resin is irradiated by curing ultraviolet radiation for 90 seconds, a curve 64 represents a spectral distribution occurring after the resin is irradiated by curing ultraviolet radiation for 120 seconds, a curve 65 represents a spectral distribution occurring after the resin is irradiated by curing ultraviolet radiation for 150 seconds, and a curve 66 represents a spectral distribution occurring after the resin is irradiated by curing ultraviolet radiation for 150 seconds and then left undisturbed for 15 days. Under the conditions of the curves 61-66, the sample 1 reaches a predetermined cure degree.

Referring to FIG. 4, the value of integral of the curves 60-66 indicates the fluorescence intensity under the respective conditions. As shown in FIG. 4, the fluorescence intensity increases due to curing while the sample is being irradiated by ultraviolet radiation and remains substantially constant thereafter (the curves 61-65). However, the fluorescence intensity increases considerably if the cured the sample 1 is left undisturbed (the curved 66). It will therefore be difficult to determine whether the sample 1 has reached a predetermined cure degree by attempting to measure the cure degree based only on the fluorescence intensity. More specifically, determination will be difficult when a certain time elapses after the sample 1 is irradiated by ultraviolet radiation. Further, since the fluorescence intensity varies depending on the amount of coating made of the sample 1, it will not be easy to determine the cure degree based only on the fluorescence intensity.

Figure 5:
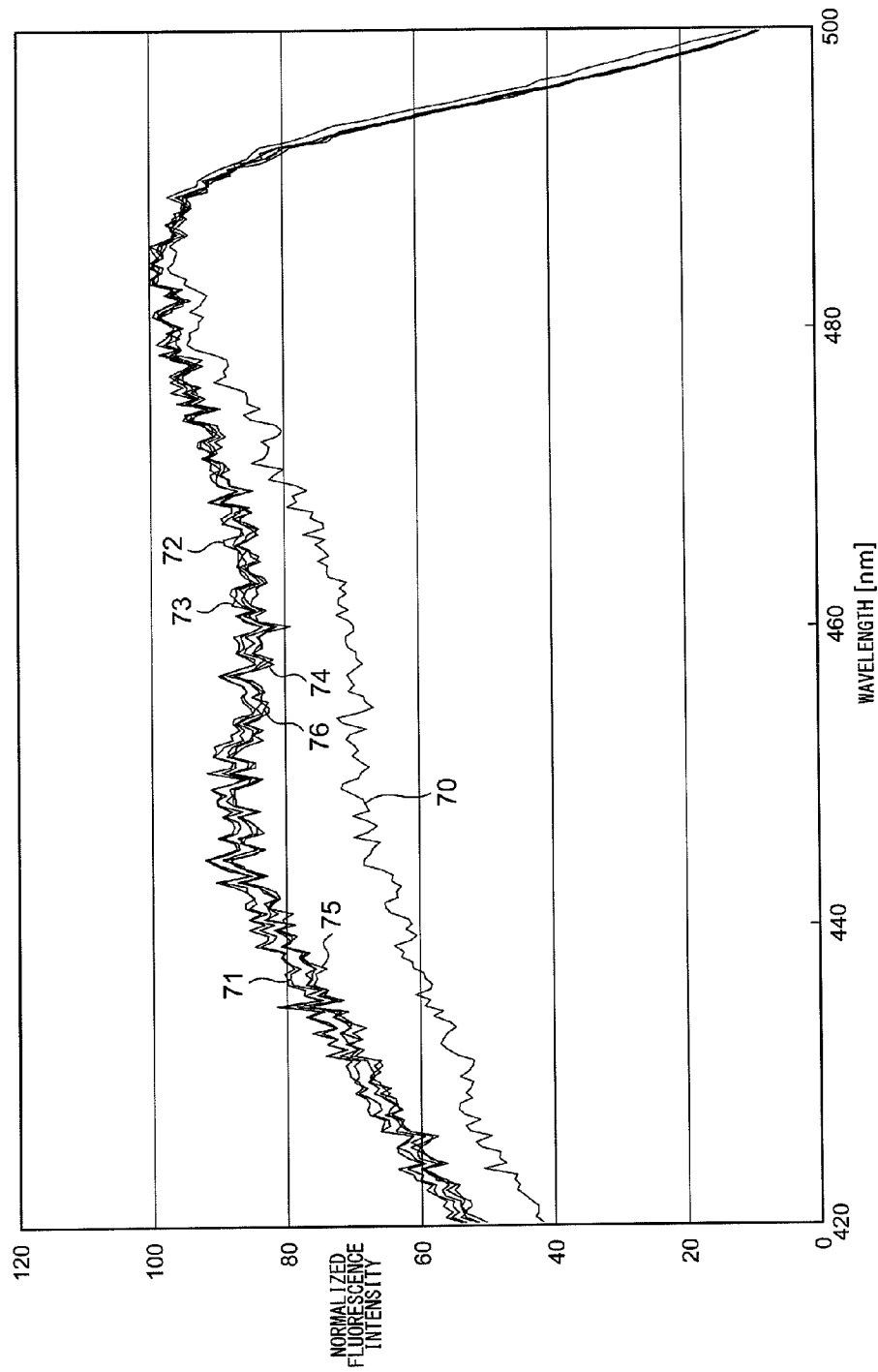
FIG. 5 shows an example in which the spectral distribution of FIG. 4 is normalized.

FIG. 5 shows an example in which the spectral distribution of FIG. 4 is normalized. FIG. 5 shows how the curves 60-66 of FIG. 4 are normalized so that the maximum fluorescence intensity is 100. Referring to FIG. 5, a curve 70 represents a normalized spectral distribution occurring before the resin is irradiated by curing ultraviolet radiation, a curve 71 represents a normalized spectral distribution occurring after the resin is irradiated by curing ultraviolet radiation for 30 seconds, a curve 72 represents a normalized spectral distribution occurring after the resin is irradiated by curing ultraviolet radiation for 60 seconds, a curve 73 represents a normalized spectral distribution occurring after the resin is irradiated by curing ultraviolet radiation for 90 seconds, a curve 74 represents a normalized spectral distribution occurring after the resin is irradiated by curing ultraviolet radiation for 120 seconds, a curve 75 represents a normalized spectral distribution occurring after the resin is irradiated by curing ultraviolet radiation for 150 seconds, and a curve 76 represents a normalized spectral distribution occurring after the resin is irradiated by curing ultraviolet radiation for 150 seconds and then left undisturbed for 15 days.

As shown in FIG. 5, the spectral distribution (the curves 71-76) of the sample 1 after curing exhibits a substantially constant shape regardless of whether the sample is being irradiated by curing ultraviolet radiation or the sample is left undisturbed after curing. The shape occurring before curing (the curve 70) is markedly different from the shape occurring after curing (the curves 71-76). Therefore, a precise determination as to whether the sample 1 is cured can be made by determining whether the shape of fluorescence spectral distribution is changed from the pre-irradiation shape. Further, since the determination is made based on the shape of spectral distribution, the determination is not affected by the amount of coating made of the sample 1.

Figure 6:
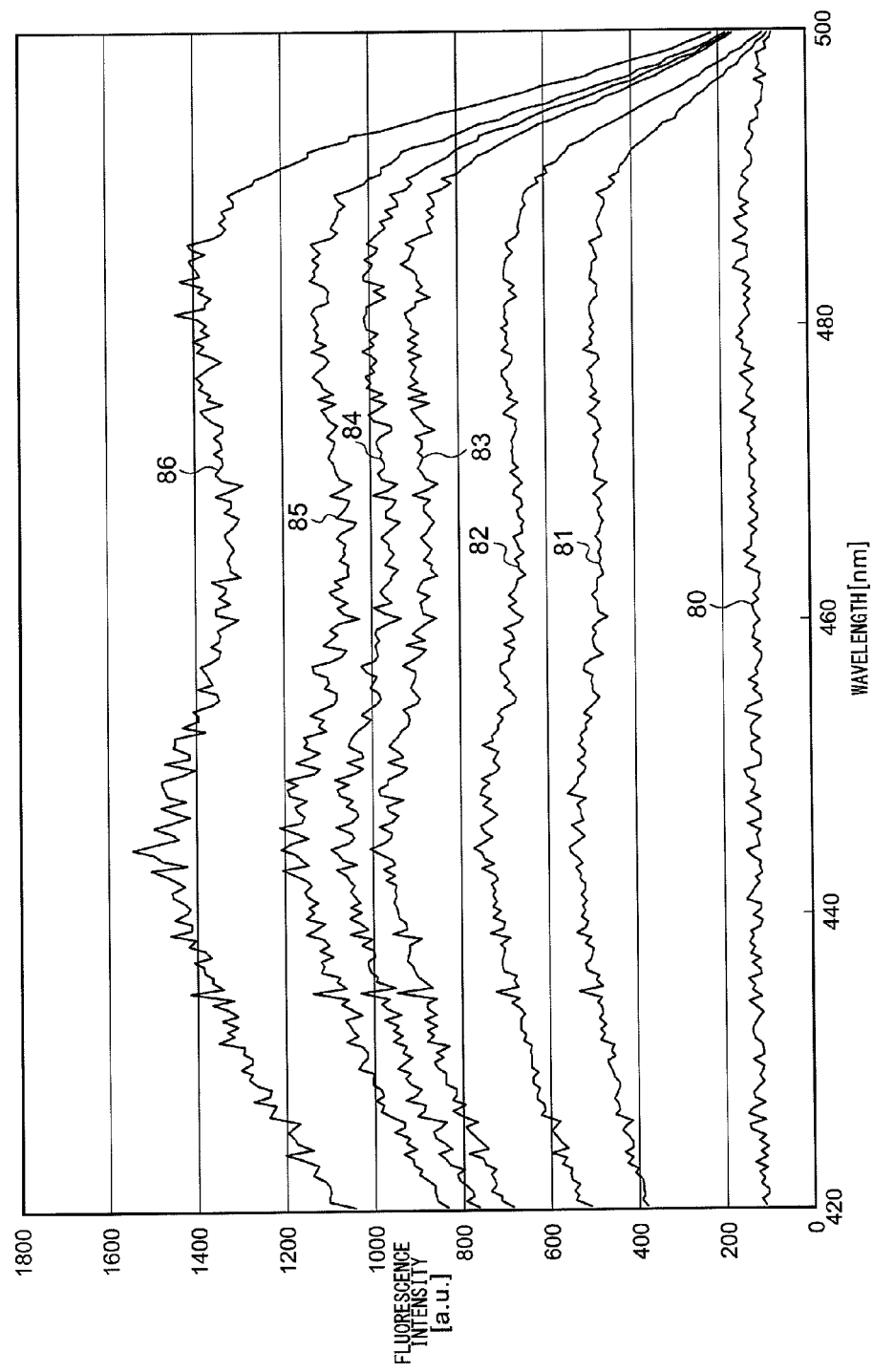
FIG. 6 shows another example of spectral distribution.

FIG. 6 shows another example of spectral distribution. FIG. 6 shows a spectral distribution obtained when the ultraviolet curable resin 52 is implemented by Optocast 3415 from Electronic Materials Inc. (hereinafter, referred to as a sample 2). Referring to FIG. 6, a curve 80 represents a spectral distribution occurring before the resin is irradiated by curing ultraviolet radiation, a curve 81 represents a spectral distribution occurring after the resin is irradiated by curing ultraviolet radiation for 30 seconds, a curve 82 represents a spectral distribution occurring after the resin is irradiated by curing ultraviolet radiation for 60 seconds, a curve 83 represents a spectral distribution occurring after the resin is irradiated by curing ultraviolet radiation for 90 seconds, a curve 84 represents a spectral distribution occurring after the resin is irradiated by curing ultraviolet radiation for 120 seconds, a curve 85 represents a spectral distribution occurring after the resin is irradiated by curing ultraviolet radiation for 150 seconds, and a curve 86 represents a spectral distribution occurring after the resin is irradiated by curing ultraviolet radiation for 150 seconds and then left undisturbed for 15 days. Under the conditions of the curves 81-86, the sample 2 reaches a predetermined cure degree.

Referring to FIG. 6, the value of integral of the curves 80-86 indicates the fluorescence intensity under the respective conditions. FIG. 6 shows that the fluorescence intensity increases with the increase in illumination in the case of the sample 2 (the curves 81-85). The graph also shows that the fluorescence intensity increases considerably by leaving the sample 2 undisturbed after curing (the curve 86). It will therefore be difficult to determine whether curing is completed by attempting to measure the cure degree of the sample 2 based only on the fluorescence intensity. Further, since the fluorescence intensity varies depending on the amount of coating made of the sample 2, it will not be easy to determine the cure degree based only on the fluorescence intensity.

Figure 7:
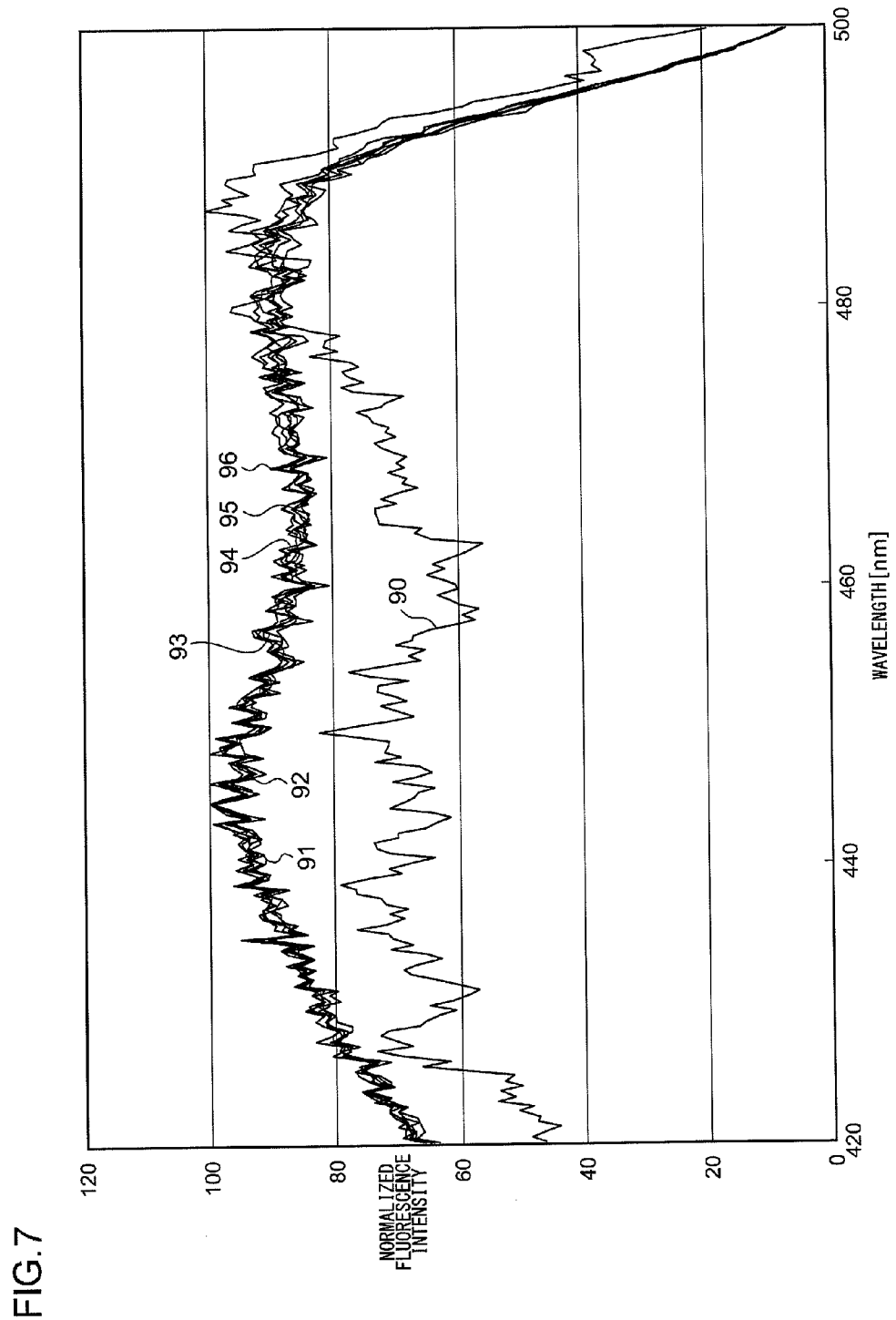
FIG. 7 shows an example in which the spectral distribution of FIG. 6 is normalized.

FIG. 7 shows an example in which the spectral distribution of FIG. 6 is normalized. FIG. 7 shows how the curves 80-86 of FIG. 6 are normalized so that the maximum fluorescence intensity is 100. Referring to FIG. 7, a curve 90 represents a normalized spectral distribution occurring before the resin is irradiated by curing ultraviolet radiation, a curve 91 represents a normalized spectral distribution occurring after the resin is irradiated by curing ultraviolet radiation for 30 seconds, a curve 92 represents a normalized spectral distribution occurring after the resin is irradiated by curing ultraviolet radiation for 60 seconds, a curve 93 represents a normalized spectral distribution occurring after the resin is irradiated by curing ultraviolet radiation for 90 seconds, a curve 94 represents a normalized spectral distribution occurring after the resin is irradiated by curing ultraviolet radiation for 120 seconds, a curve 95 represents a normalized spectral distribution occurring after the resin is irradiated by curing ultraviolet radiation for 150 seconds, and a curve 96 represents a normalized spectral distribution occurring after the resin is irradiated by curing ultraviolet radiation for 150 seconds and then left undisturbed for 15 days.

As shown in FIG. 7, the spectral distribution (the curves 91-96) of the sample 2 after curing also exhibits a substantially constant shape regardless of whether the sample is being irradiated by curing ultraviolet radiation or the sample is left undisturbed after curing. The shape occurring before curing (the curve 90) is markedly different from the shape occurring after curing (the curves 91-96). Therefore, a precise determination as to whether the sample 2 is cured can be made by determining whether the shape of fluorescence spectral distribution is changed from the pre-irradiation shape. Since the determination is made based on the shape of spectral distribution, the determination is not affected by the amount of coating made of the sample 2.

Figure 8:
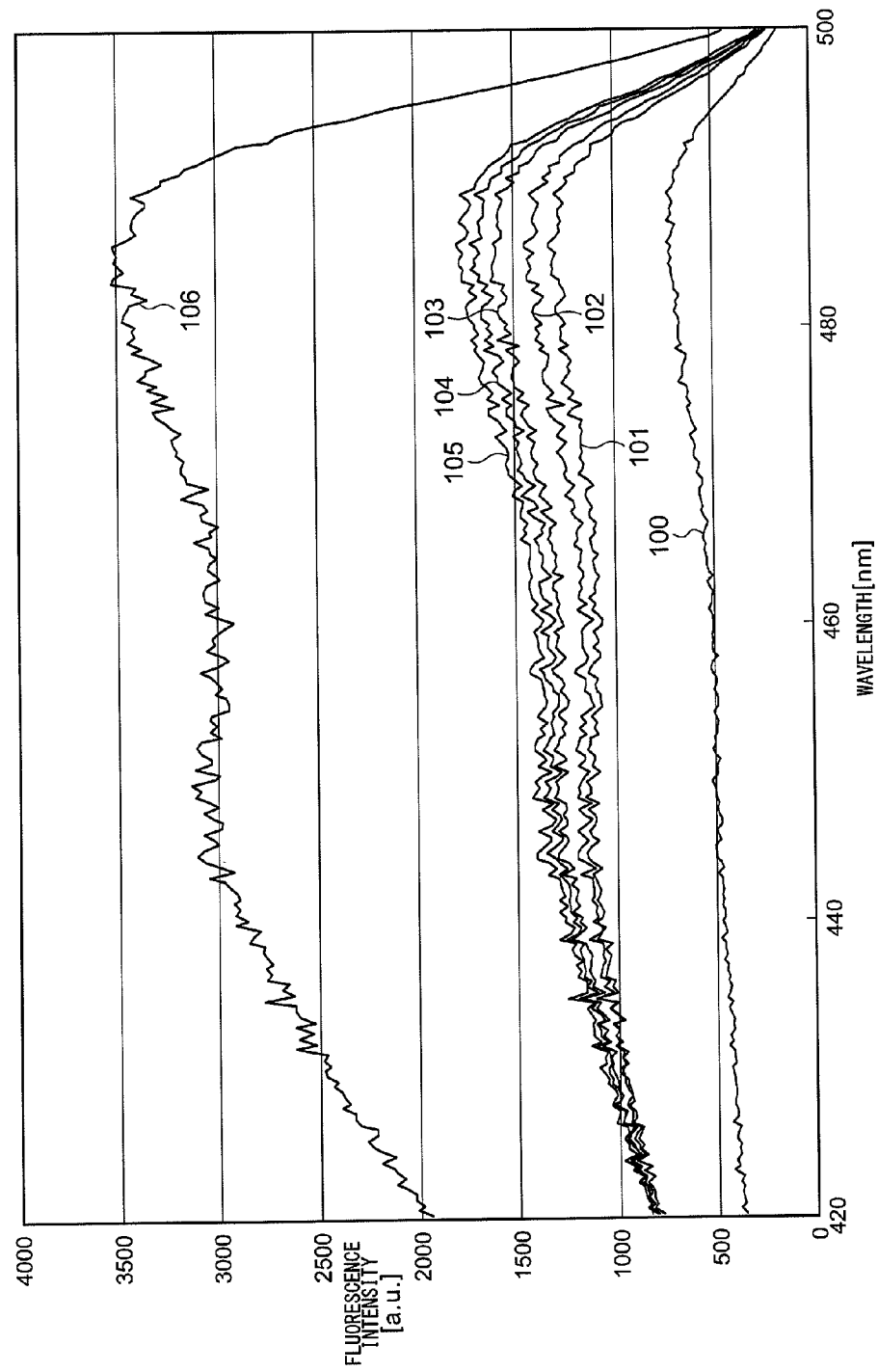
FIG. 8 shows still another example of spectral distribution.

FIG. 8 shows still another example of spectral distribution. FIG. 8 shows a spectral distribution obtained when the ultraviolet curable resin 52 is implemented by using Chemiseal 426B from Chemitech Inc. (hereinafter, referred to as a sample 3). Referring to FIG. 8, a curve 100 represents a spectral distribution occurring before the resin is irradiated by curing ultraviolet radiation, a curve 101 represents a spectral distribution occurring after the resin is irradiated by curing ultraviolet radiation for 30 seconds, a curve 102 represents a spectral distribution occurring after the resin is irradiated by curing ultraviolet radiation for 60 seconds, a curve 103 represents a spectral distribution occurring after the resin is irradiated by curing ultraviolet radiation for 90 seconds, a curve 104 represents a spectral distribution occurring after the resin is irradiated by curing ultraviolet radiation for 120 seconds, a curve 105 represents a spectral distribution occurring after the resin is irradiated by curing ultraviolet radiation for 150 seconds, and a curve 106 represents a spectral distribution occurring after the resin is irradiated by curing ultraviolet radiation for 150 seconds and then left undisturbed for 15 days. Under the conditions of the curves 101-106, the sample 3 reaches a predetermined cure degree.

Referring to FIG. 8, the value of integral of the curves 100-106 indicates the fluorescence intensity under the respective conditions. As shown in FIG. 8, the fluorescence intensity increases due to curing while the sample 3 is being irradiated by ultraviolet radiation and remains substantially, if not completely, constant thereafter (the curves 101-105). However, the fluorescence intensity increases considerably by leaving the cured sample 3 undisturbed (the curve 106). It will therefore be difficult to determine whether the sample 3 has reached a predetermined cure degree by attempting to measure the cure degree based only on the fluorescence intensity. More specifically, determination will be difficult when a certain time elapses after the sample 3 is irradiated by curing ultraviolet radiation. Further, since the fluorescence intensity varies depending on the amount of coating made of the sample 3, it will not be easy to determine the cure degree based only on the fluorescence intensity.

Figure 9:
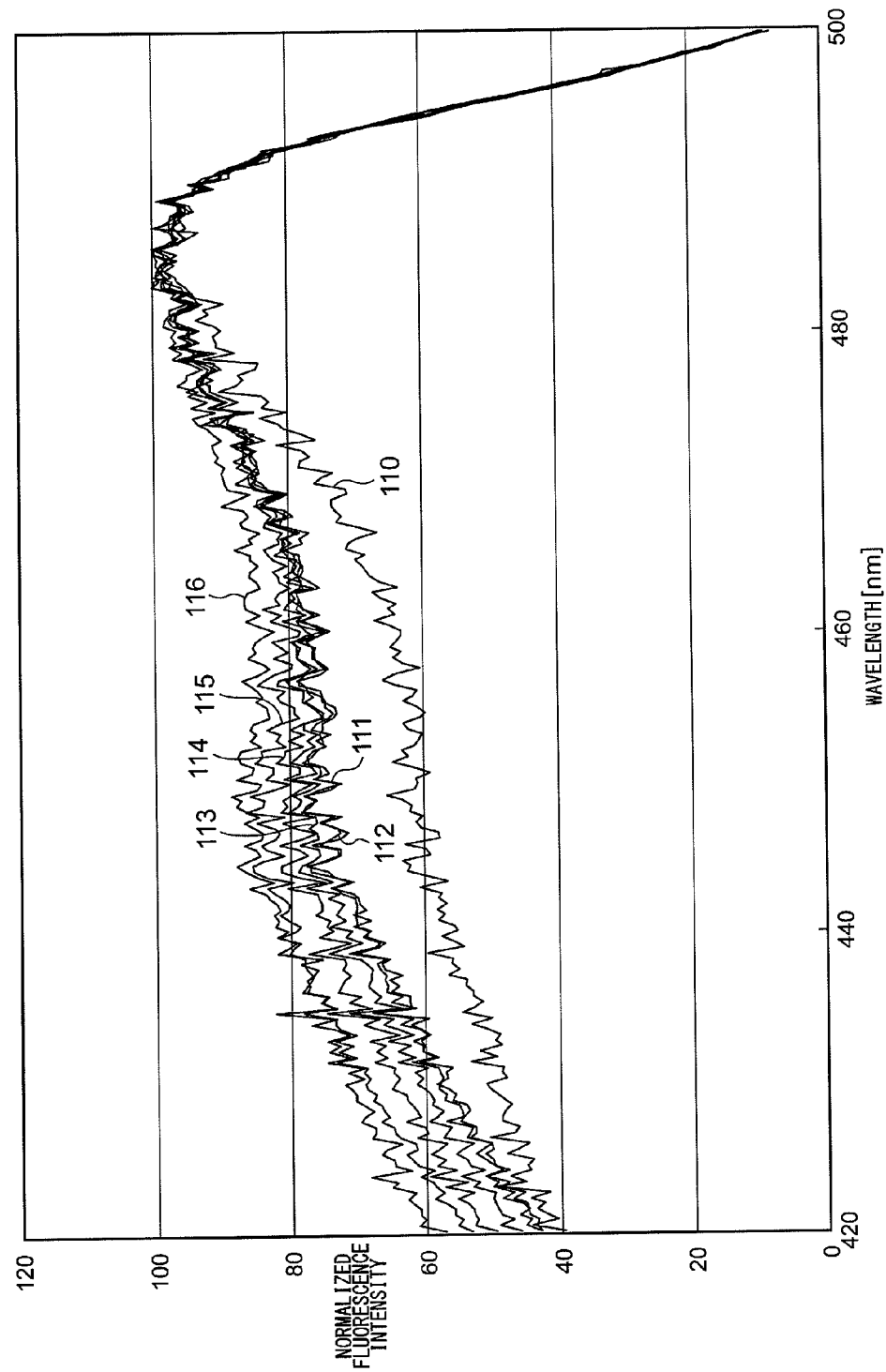
FIG. 9 shows an example in which the spectral distribution of FIG. 8 is normalized.

FIG. 9 shows an example in which the spectral distribution of FIG. 8 is normalized. FIG. 9 shows how the curves 100-106 of FIG. 8 are normalized so that the maximum fluorescence intensity is 100. Referring to FIG. 9, a curve 110 represents a normalized spectral distribution occurring before the resin is irradiated by curing ultraviolet radiation, a curve 111 represents a normalized spectral distribution occurring after the resin is irradiated by curing ultraviolet radiation for 30 seconds, a curve 112 represents a normalized spectral distribution occurring after the resin is irradiated by curing ultraviolet radiation for 60 seconds, a curve 113 represents a normalized spectral distribution occurring after the resin is irradiated by curing ultraviolet radiation for 90 seconds, a curve 114 represents a normalized spectral distribution occurring after the resin is irradiated by curing ultraviolet radiation for 120 seconds, a curve 115 represents a normalized spectral distribution occurring after the resin is irradiated by curing ultraviolet radiation for 150 seconds, and a curve 116 represents a normalized spectral distribution occurring after the resin is irradiated by curing ultraviolet radiation for 150 seconds and then left undisturbed for 15 days.

As shown in FIG. 9, the spectral distribution (the curves 111-116) of the sample 3 after curing exhibits a substantially constant shape regardless of whether the sample is being irradiated by curing ultraviolet radiation or the sample is left undisturbed after curing. The shape occurring before curing (the curve 110) is markedly different from the shape occurring after curing (the curves 111-116). Therefore, a precise determination as to whether the sample 3 is cured can be made by determining whether the shape of fluorescence spectral distribution is changed from the pre-irradiation shape. Further, since the determination is made based on the shape of spectral distribution, the determination is not affected by the amount of coating made of the sample 3.

Figure 10:
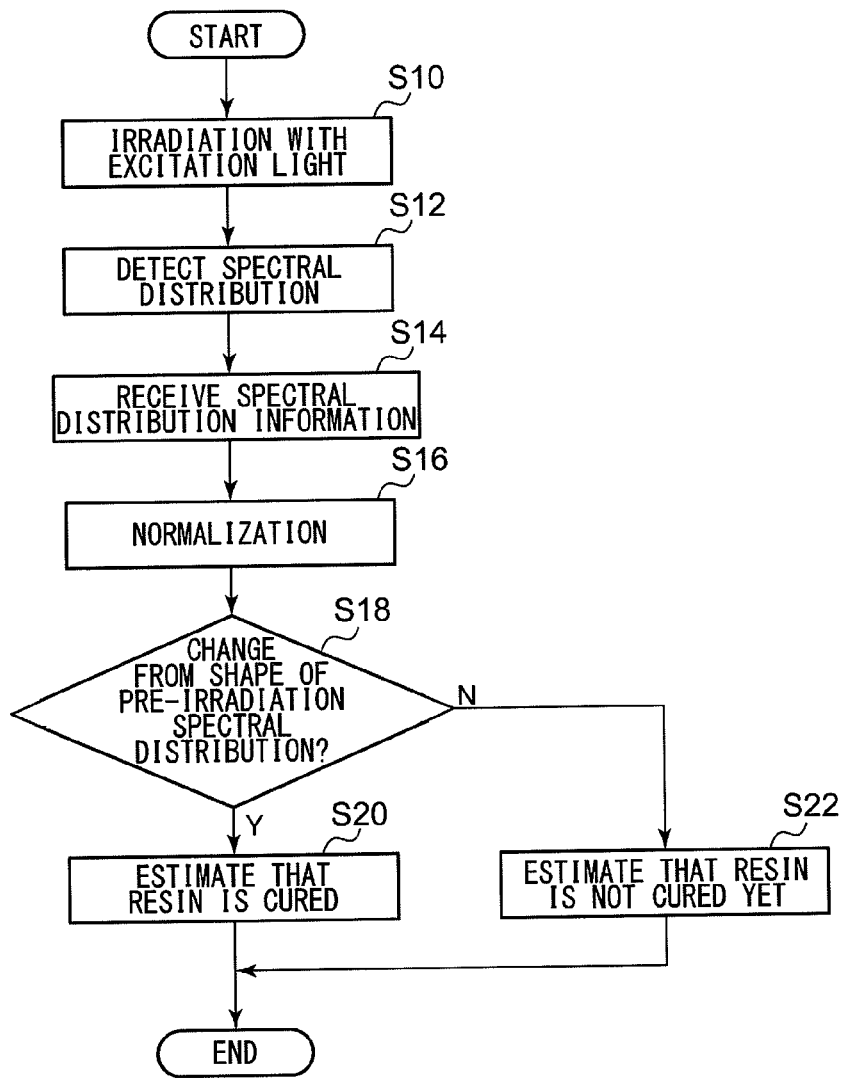
FIG. 10 is a flowchart for the status estimation device according to the first embodiment.

FIG. 10 is a flowchart for the status estimation device 10 according to the first embodiment. To estimate the status of the ultraviolet curable resin 52 using the status estimation device 10, the excitation LED 12 is first lighted so as to irradiate the excitation light from the probe 18 onto the ultraviolet curable resin 52 (S10). Fluorescence produced from the ultraviolet curable resin 52 is incident on the probe 18 and incident on the spectroscope 16 via the second optical fiber 22, the wavelength demultiplexer 14, and the third optical fiber 24.

The spectroscope 16 detects the spectral distribution of fluorescence received (S12). Information on the detected spectral distribution is sent to the computer 50 so that the receiver unit 54 of the computer 50 receives the information (S14). The received spectral distribution information is sent to the normalization unit 56.

The normalization unit 56 normalizes the spectral distribution (S16). The method of normalization is non-limiting. For example, normalization is performed such that maximum fluorescence intensity is 100, as shown in FIGS. 5, 7, and 9. Information on the normalized spectral distribution is sent to the estimation unit 58.

The estimation unit 58 compares the previously stored normalized pre-irradiation spectral distribution with the spectral distribution (post-irradiation spectral distribution) received from the normalization unit 56 and determines whether the shape of post-irradiation spectral distribution is changed from the pre-irradiation shape (S18).

If the shape of the post-irradiation spectral distribution is changed from the pre-irradiation shape to exhibit a different shape (Y in S18), the estimation unit 58 estimates that the ultraviolet curable resin 52 has reached a predetermined cure degree, i.e., that the resin is cured (S20). Meanwhile, if the shape of the post-irradiation spectral distribution is not changed from the pre-irradiation shape (N in S18), the estimation unit 58 estimates that the ultraviolet curable resin 52 has not reached a predetermined cure degree, i.e., the resin is not cured yet (S22).

As described above, according to the status estimation device 10 of the first embodiment, the cure degree of the ultraviolet curable resin 52 can be determined with high precision even when a certain time elapses after curing, by estimating the status of the ultraviolet curable resin 52 based on the shape of spectral distribution. Further, according to the status estimation device 10, precision of the measurement of cure degree is not affected by the amount of coating made of the ultraviolet curable resin 52. The degree of variation in the shape of spectral distribution that warrants determination of the completion of curing varies depending on, for example, the type of ultraviolet curable resin 52 used. Therefore, the criterion may be defined through experiments or the like.

In the first embodiment, the estimation unit 58 of the computer 50 compares the pre-irradiation spectral distribution with the post-irradiation spectral distribution. Alternatively, a personnel responsible for measurement may compare the pre-irradiation spectral distribution and the post-irradiation spectral distribution as displayed so as to determine whether the shapes match or not.

The estimation unit 58 of the computer 50 may alternatively estimate that the ultraviolet curable resin has reached a predetermined cure degree if the post-irradiation spectral distribution is of a predetermined shape. The "predetermined shape" may be provided in the form of data. Alternatively, the spectral distribution of a sample already cured may be measured and the result of measurement may be stored in a memory of the computer 50 for use. In this case, precision of determination of cure degree can be improved.

According to the first embodiment, the spectral distribution is normalized to facilitate comparison between shapes. Alternatively, the status of the ultraviolet curable resin 52 may be estimated based on the shape of normalized spectral distribution.

For efficient demultiplexing in the spectroscope 16 using a grating or LVF, it is necessary to create collimating lights of a small beam diameter. For this purpose, the light may be temporarily captured in a small area like an optical fiber. This facilitates production of collimating lights having a small beam diameter. For this purpose, the embodiment is advantageous in that an optical fiber is used as a path of fluorescence.

Figure 11:
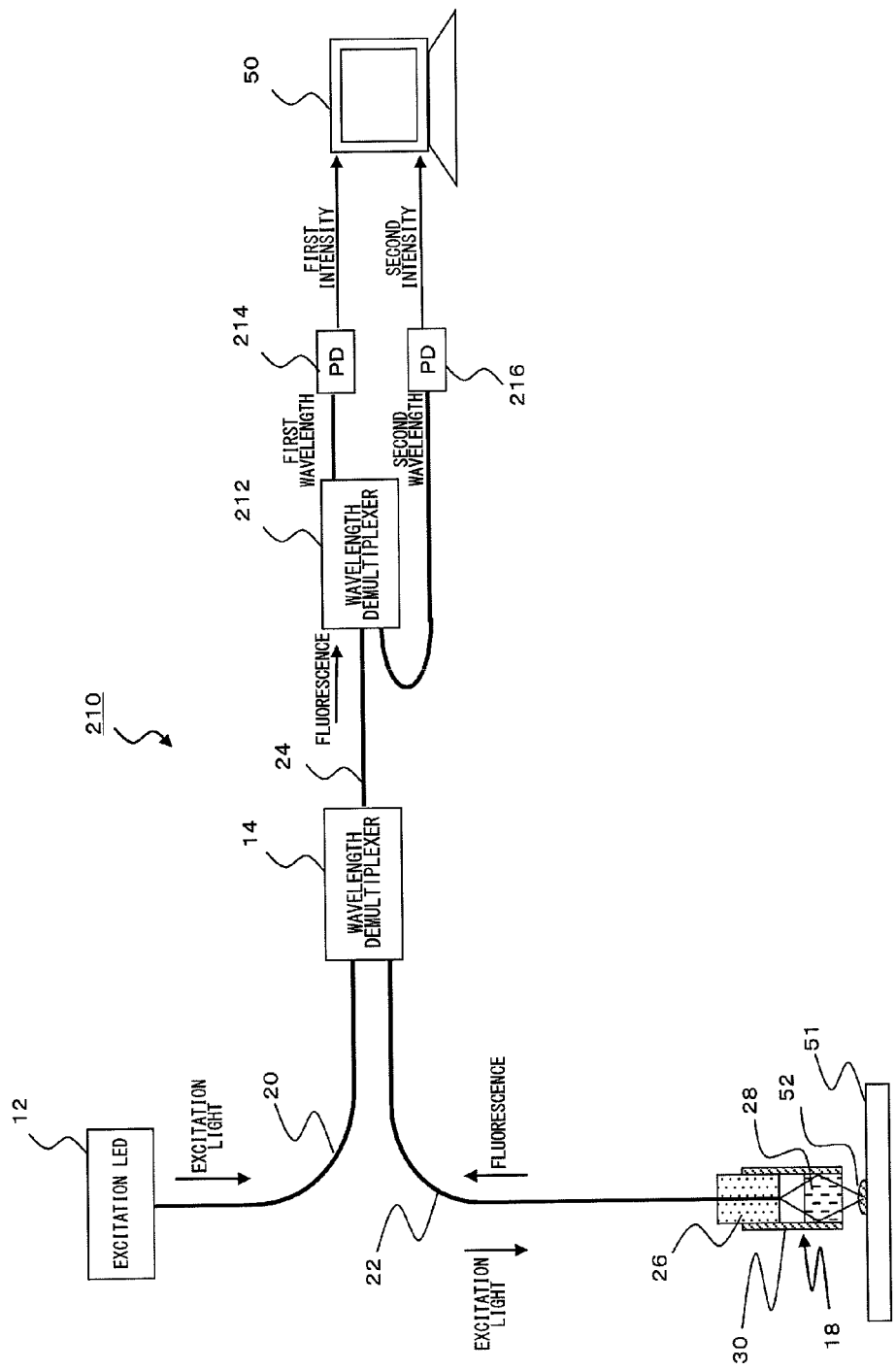
FIG. 11 shows the ultraviolet curable resin status estimation device according to the second embodiment of the present invention.

FIG. 11 shows an ultraviolet curable resin status estimation device 210 according to the second embodiment of the present invention. In the status estimation device 210 shown in FIG. 11, the spectroscope 16 in the status estimation device 10 shown in FIG. 1 is replaced by a wavelength demultiplexer 212, a first photodiode 214, and a second photodiode 216. In the status estimation device 210 according to the second embodiment, those components that are identical or corresponding to the components of the status estimation device 10 according to the first embodiment may be denoted by identical symbols and the description of the components is omitted as appropriate.

As shown in FIG. 11, the wavelength demultiplexer 14 is connected to the wavelength demultiplexer 212 via the third optical fiber 24. The wavelength demultiplexer 212 demultiplexes the fluorescence incident from the third optical fiber 24 into the fluorescence of the first wavelength and that of the second wavelength, outputting them to the first photodiode 214 and the second photodiode 216, respectively. The first wavelength and the second wavelength differ from each other. For example, if the sample 1 is used as the ultraviolet curable resin 52, the wavelength demultiplexer 212 demultiplexes the input fluorescence into the fluorescence with a wavelength 480-490 nm centered around the first wavelength=485 nm, and the fluorescence with a wavelength 440-450 nm centered around the second wavelength=445 nm.

The first photodiode 214 supplied with the fluorescence with the first wavelength converts the fluorescence with the first wavelength into an electrical signal and outputs the signal to the computer 50 as first intensity information. The second photodiode 216 supplied with the fluorescence of the second wavelength converts the fluorescence with the second wavelength into an electrical signal and outputs the signal to the computer 50 as second intensity information.

Figure 12:
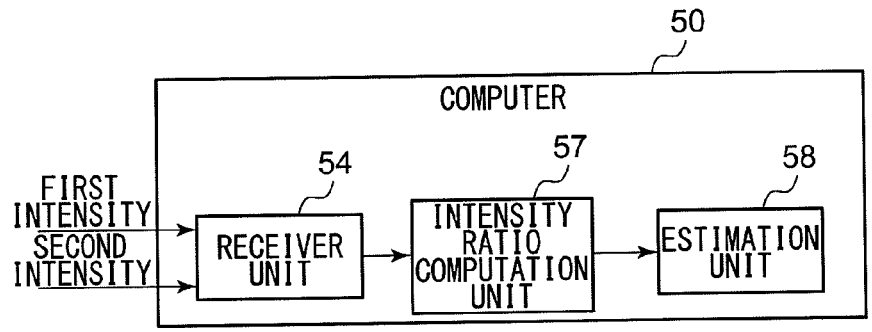
FIG. 12 shows functional blocks of the computer according to the second embodiment.

FIG. 12 shows functional blocks of the computer 50 according to the second embodiment. As shown in FIG. 12, the computer 50 comprises a receiver unit 54, an intensity ratio computation unit 57, and an estimation unit 58.

The receiver 54 receives the first intensity information and the second intensity information from the first photodiode 214 and the second photodiode 216, respectively. The intensity ratio computation unit 57 computes the intensity ratio of the first intensity with respect to the second intensity. The estimation unit 58 estimates the status of the ultraviolet curable resin 52 based on the intensity ratio computed by the intensity ratio computation unit 57.

More specifically, the estimation unit 58 compares the pre-irradiation intensity ratio detected when the pre-irradiation ultraviolet curable resin 52 is illuminated by the excitation light with post-irradiation intensity ratio detected when the post-irradiation ultraviolet curable resin 52 is illuminated by the excitation light. If the post-irradiation intensity ratio differs in value from the pre-irradiation intensity ratio, the estimation unit 58 estimates that the ultraviolet curable resin has reached a predetermined cure degree. The pre-irradiation intensity ratio may be stored in the computer 50 before the comparison.

Figure 13:
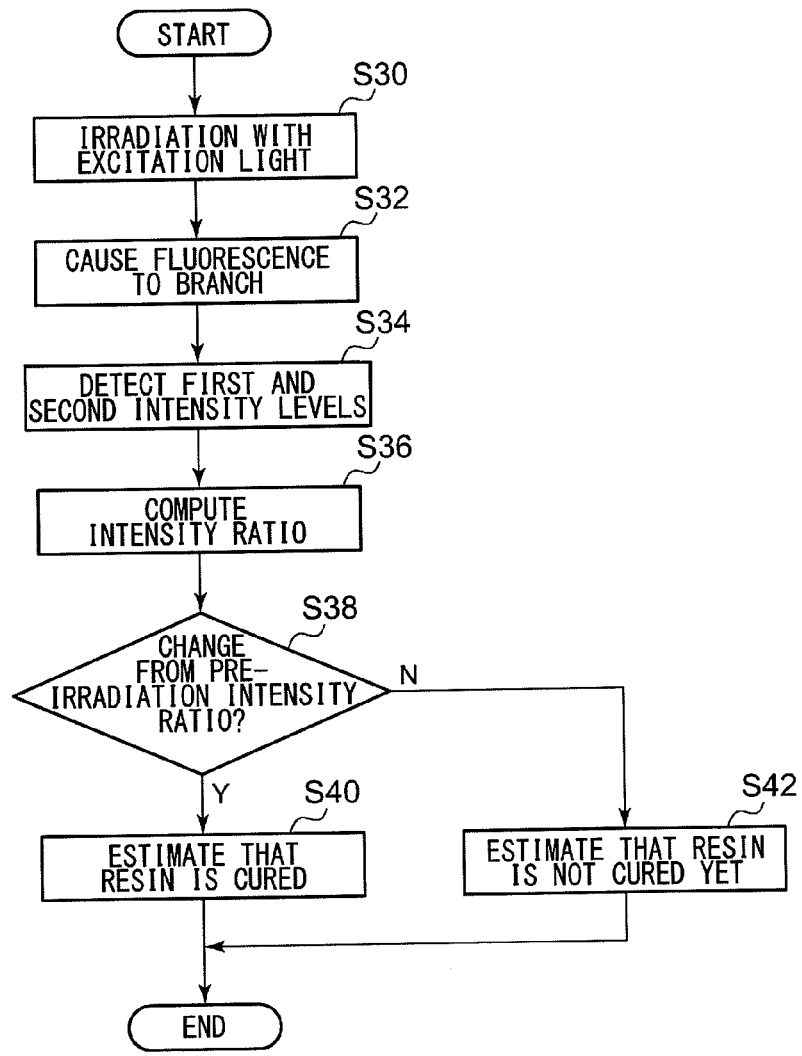
FIG. 13 is a flowchart for the status estimation device according to the second embodiment.

FIG. 13 is a flowchart for the status estimation device 210 according to the second embodiment. To estimate the status of the ultraviolet curable resin 52 using the status estimation device 210, the excitation LED 12 is first lighted so as to irradiate the excitation light from the probe 18 onto the ultraviolet curable resin 52 (S30). Fluorescence produced from the ultraviolet curable resin 52 is incident on the probe 18 and incident on the wavelength demultiplexer 212 via the second optical fiber 22, the wavelength demultiplexer 14, and the third optical fiber 24.

The wavelength demultiplexer 212 demultiplexes the received fluorescence into the fluorescence with the first wavelength and the fluorescence with the second wavelength (S32). The fluorescence with the first wavelength resulting from the wavelength demultiplexer is received by the first photodiode 214 which detects the first intensity. The fluorescence with the second wavelength is received by the second photodiode 216 which detects the second intensity (S34). The first intensity and the second intensity are received by the receiver unit 54 of the computer 50.

Subsequently, the intensity ratio computation unit 57 computes the intensity ratio of the second intensity with respect to the first intensity (S36). For example, as shown in FIG. 4, the fluorescence intensity at the first wavelength=485 nm occurring after the sample 1 is irradiated by curing ultraviolet radiation for 30 seconds is 1265, and the fluorescence intensity at the second wavelength=445 nm is 1133. Therefore, the intensity ratio is 0.89. Further, the fluorescence intensity at the first wavelength=485 nm occurring when the sample 1 is irradiated by curing ultraviolet radiation for 150 seconds and then left undisturbed is 2020, and the fluorescence intensity at the second wavelength=445 nm is 1776. Therefore, the intensity ratio is 0.88. The computed intensity ratio information is sent to the estimation unit 58.

The estimation unit 58 compares the previously stored pre-irradiation intensity ratio with the intensity ratio received from the intensity ratio computation unit 57 (post-irradiation intensity ratio) and determines whether the post-irradiation intensity ratio is changed from the pre-irradiation intensity ratio (S38). For example, as shown in FIG. 4, the fluorescence intensity at the first wavelength=485 nm occurring before the sample 1 is irradiated by curing ultraviolet radiation is 118, and the fluorescence intensity at the second wavelength=445 nm is 87. Therefore, the intensity ratio is 0.74.

If the post-irradiation intensity ratio differs in value from the pre-irradiation intensity ratio (Y in S38), the estimation unit 58 estimates that the ultraviolet curable resin 52 has reached a predetermined cure degree (S40). For example, the intensity ratio occurring after the sample 1 is irradiated by ultraviolet radiation for 30 seconds is 0.89, which is different in value from the pre-irradiation intensity ratio=0.74. Therefore, it is estimated that the resin has reached a predetermined cure degree. Further, the intensity ratio occurring after the resin is irradiated by ultraviolet radiation for 150 seconds and then left undisturbed is 0.88, which is also different in value from the pre-irradiation intensity ratio=0.74. Therefore, it is estimated that the resin has reached a predetermined cure degree. Meanwhile, if the post-irradiation intensity ratio is not changed from the pre-irradiation intensity ratio (N in S38), the estimation unit 58 estimates that the ultraviolet curable resin 52 has not reached a predetermined cure degree, i.e., that the resin is not cured yet (S42).

As described above, the status estimation device 210 according to the second embodiment is configured to estimate the status of the ultraviolet curable resin 52 based on the intensity ratio between fluorescence intensity levels at two different wavelengths. Since the intensity ratio occurring when a certain time elapses after curing is substantially unchanged from the intensity ratio occurring while the resin is being irradiated by curing ultraviolet radiation, the cure degree of the ultraviolet resin 52 can be determined with high precision. In further accordance with the status estimation device 210, precision of measurement of cure degree is not affected by the amount of coating made of the ultraviolet curable resin 52. The degree of variation in the intensity ratio that warrants determination of the completion of curing varies depending on, for example, the type of ultraviolet curable resin 52 used. Therefore, the criterion may be defined through experiments or the like.

In the second embodiment, the estimation unit 58 of the computer 50 compares the pre-irradiation intensity ratio with the post-irradiation intensity ratio. Alternatively, a personnel responsible for measurement may compare the pre-irradiation intensity ratio with the post-irradiation intensity ratio so as to determine whether the ultraviolet curable resin 52 has reached a predetermined cure degree.

Further, the estimation unit 58 of the computer 50 may estimate that the ultraviolet curable resin has reached a predetermined cure degree if the post-irradiation spectral distribution exhibits a predetermined intensity ratio. The "predetermined intensity ratio" may be provided in the form of data. Alternatively, the intensity ratio of a sample already cured may be measured and the result of measurement may be stored in a memory of the computer 50 for use. In this case, precision of determination of cure degree can be improved.

Described above is an explanation based on an exemplary embodiment. The embodiment is intended to be illustrative only and it will be obvious to those skilled in the art that various modifications to constituting elements and processes could be developed and that such modifications are also within the scope of the present invention.

For example, the excitation LED 12 may be lighted at a frequency of about 100 Hz-10 kHz to detect only the fluorescence components in the frequency range. For example, a lock-in circuit may be provided in the spectroscope 16 of the first embodiment and the fluorescence may be detected in synchronization with the lighting of the excitation LED 12. Alternatively, FFT may be used to obtain the signal intensity of the components in the frequency range. This allows more sensitive measurement not affected by ambient light. In the above-described structure, it is desirable to employ the spectroscope 16 implemented by using an LVF.

In the embodiments described above, an optical fiber is used as a path of transmitting excitation light or fluorescence. Transmission paths may be configured otherwise. For example, a light waveguide may be used. Still alternatively, excitation light or fluorescence may be transmitted by using spatial light transmission.

What is claimed is:

1. A status estimation device for ultraviolet curable resin comprising:
    an excitation light source that emits excitation light;
    a first wavelength demultiplexer connected to the excitation light source via a first optical fiber;
    a probe connected to the first wavelength demultiplexer via a second optical fiber;
    a second wavelength demultiplexer connected to the first wavelength demultiplexer via a third optical fiber;
    a first detection unit connected to the second wavelength demultiplexer via a fourth optical fiber;
    a second detection unit connected to the second wavelength demultiplexer via a fifth optical fiber; and
    an estimation unit connected to the first detection unit and the second detection unit, wherein
    the first wavelength demultiplexer guides the excitation light incident from the first optical fiber to the second optical fiber,
    the probe irradiates the ultraviolet curable resin with the excitation light incident from the second optical fiber, receives fluorescence produced from the ultraviolet curable resin, and guides the fluorescence to the second optical fiber,
    the first wavelength demultiplexer guides the fluorescence incident from the second optical fiber to the third optical fiber,
    the second wavelength demultiplexer demultiplexes the fluorescence incident from the third optical fiber into the fluorescence of the first wavelength and that of the second wavelength, outputs the fluorescence of the first wavelength to the first detection unit via the fourth optical fiber, and outputs the fluorescence of the second wavelength to the second detection unit via the fifth optical fiber,
    the first detection unit detects a first intensity at the first wavelength of the fluorescence and the second detection unit detects a second intensity at the second wavelength of the fluorescence, and
    the estimation unit estimates the status of the ultraviolet curable resin based on the intensity ratio of the second intensity with respect to the first intensity,
    wherein the status estimation device includes a single probe.

2. The status estimation device for ultraviolet curable resin according to claim 1,
    wherein the estimation unit estimates the status of the ultraviolet curable resin by comparing pre-irradiation intensity ratio detected when the ultraviolet curable resin is irradiated by excitation light before being irradiated by ultraviolet radiation with post-irradiation intensity ratio detected when the ultraviolet curable resin is irradiated by excitation light after being irradiated by ultraviolet radiation.

3. The status estimation device for ultraviolet curable resin according to claim 1,
    wherein the estimation unit estimates that the ultraviolet curable resin has reached a predetermined cure degree if the post-irradiation intensity ratio detected when the ultraviolet curable resin is irradiated by excitation light after being irradiated by ultraviolet radiation is a predetermined intensity ratio.

4. The status estimation device according to claim 1, wherein
    the excitation light source is lighted at a predetermined frequency to emit excitation light, and
    the first detection unit and the second detection unit detects only fluorescence components of the predetermined frequency.

5. The status estimation device according to claim 1, wherein
    the first wavelength is in a range 480-490 nm and the second wavelength is in a range 440-450 nm.

6. The status estimation device for ultraviolet curable resin according to claim 2,
    the estimation unit estimates that the ultraviolet curable resin has reached a predetermined cure degree if the post-irradiation intensity ratio differs in value from the pre-irradiation intensity ratio.

7. The status estimation device according to claim 2, wherein
    the estimation unit includes a memory for storing the pre-irradiation intensity ratio detected when the ultraviolet curable resin is irradiated by excitation light before being irradiated by ultraviolet radiation.

8. A status estimation method for ultraviolet curable resin using a status estimation device that comprises:
    an excitation light source that emits excitation light;
    a first wavelength demultiplexer connected to the excitation light source via a first optical fiber;
    a probe connected to the first wavelength demultiplexer via a second optical fiber;
    a second wavelength demultiplexer connected to the first wavelength demultiplexer via a third optical fiber;
    a first detection unit connected to the second wavelength demultiplexer via a fourth optical fiber; and
    a second detection unit connected to the second wavelength demultiplexer via a fifth optical fiber,
    the method comprising:
    guiding, using the first wavelength demultiplexer, the excitation light incident from the first optical fiber to the second optical fiber;
    irradiating, using the probe, the ultraviolet curable resin with excitation light incident from the second optical fiber, receiving fluorescence produced from the ultraviolet curable resin, and guiding the fluorescence to the second optical fiber;
    guiding, using the first wavelength demultiplexer, the fluorescence incident from the second optical fiber to the third optical fiber;
    demultiplexing, using the second wavelength demultiplexer, the fluorescence incident from the third optical fiber into the fluorescence of the first wavelength and that of the second wavelength, outputting the fluorescence of the first wavelength to the first detection unit via the fourth optical fiber, and outputting the fluorescence of the second wavelength to the second detection unit via the fifth optical fiber;

detecting, using the first detection unit, a first intensity at the first wavelength of the fluorescence;

detecting, using the second detection unit, a second intensity at the second wavelength of the fluorescence; and estimating the status of the ultraviolet curable resin based on the intensity ratio of the second intensity with respect to the first intensity, wherein the status estimation device includes a single probe.

9. The status estimation method for ultraviolet curable resin according to claim 8, wherein the estimating includes estimating the status of the ultraviolet curable resin by comparing pre-irradiation intensity ratio detected when the ultraviolet curable resin is irradiated by excitation light before being irradiated by ultraviolet radiation with post-irradiation intensity ratio detected when the ultraviolet curable resin is irradiated by excitation light after being irradiated by ultraviolet radiation.

10. The status estimation method for ultraviolet curable resin according to claim 8, wherein the estimating includes estimating that the ultraviolet curable resin has reached a predetermined cure degree if the post-irradiation intensity ratio detected when the ultraviolet curable resin is irradiated by excitation light after being irradiated by ultraviolet radiation is a predetermined intensity ratio.

11. The status estimation method for ultraviolet curable resin according to claim 9, the estimating includes estimating that the ultraviolet curable resin has reached a predetermined cure degree if the post-irradiation intensity ratio differs in value from the pre-irradiation intensity ratio.

* * * * *